United States Patent [19]

Niira, deceased et al.

[11] Patent Number: 4,938,958

[45] Date of Patent: * Jul. 3, 1990

[54] ANTIBIOTIC ZEOLITE

[75] Inventors: Reiji Niira, deceased, late of Kokubunki, by Yuriko Niira, legal representative, Yuriko Niira, Kiyotaka Niira, Hideaki Niira, legal heirs; Tatuo Yamamoto, Inazawa; Masashi Uchida, Nagoya, all of Japan

[73] Assignees: Shinagawa Fuel Co., Ltd.; Shinanen New Ceramic Corporation, both of Japan

[*] Notice: The portion of the term of this patent subsequent to Jul. 3, 2007 has been disclaimed.

[21] Appl. No.: 127,645

[22] Filed: Dec. 2, 1987

[30] Foreign Application Priority Data

Dec. 5, 1986 [JP] Japan .................. 61-290144

[51] Int. Cl.$^5$ ............ A61K 31/74; A01N 59/16; A01N 59/20; A01N 59/00

[52] U.S. Cl. ..................... 424/79; 424/618; 424/630; 424/641; 424/688; 424/617; 424/719; 523/122; 521/25; 521/63; 524/450

[58] Field of Search ............ 424/79, 132, 140, 145, 424/157, 131, 166; 523/122; 521/25, 63; 524/450

[56] References Cited

U.S. PATENT DOCUMENTS 4,525,410  6/1985  Hagriweira et al. ............ 424/132

FOREIGN PATENT DOCUMENTS

| 23546 | 7/1984 | Australia . | |
|---|---|---|---|
| 61818 | 5/1986 | Australia . | |
| 13-4422 | of 1938 | Japan . | |
| 52-92000 | of 1977 | Japan . | |
| 55-38358 | of 1980 | Japan . | |
| 55-164236 | of 1980 | Japan . | |
| 57-77022 | of 1982 | Japan . | |
| 59-37956 | 8/1984 | Japan . | |
| 59-133235 | 9/1984 | Japan . | |
| 60-64611 | of 1985 | Japan . | |
| 60-178810 | of 1985 | Japan . | |
| 60-181002 | of 1985 | Japan . | |
| 60-184325 | of 1985 | Japan . | |
| 60-202162 | of 1985 | Japan . | |
| 60-174707 | 3/1985 | Japan . | |
| 60-181370 | 5/1985 | Japan . | |
| 60-79433 | 9/1985 | Japan . | |
| 60-136796 | 11/1985 | Japan . | |
| 60-100504 | 12/1985 | Japan . | |
| 60-136795 | 12/1985 | Japan . | |
| 61-137564 | of 1986 | Japan . | |
| 61-138647 | of 1986 | Japan . | |
| 61-138658 | of 1986 | Japan . | |
| 61-138795 | of 1986 | Japan . | |
| 61-103401 | 3/1986 | Japan . | |
| 61-232253 | 10/1986 | Japan | 523/122 |
| 62-7746 | of 1987 | Japan . | |
| 62-7747 | of 1987 | Japan . | |
| 62-41775 | of 1987 | Japan . | |
| 62-70221 | of 1987 | Japan . | |
| 62-195037 | of 1987 | Japan . | |
| 62-195038 | of 1987 | Japan . | |
| 62-238900 | of 1987 | Japan . | |
| 62-241932 | of 1987 | Japan . | |
| 62-241939 | of 1987 | Japan . | |
| 62-243665 | of 1987 | Japan . | |
| 62-7748 | 1/1987 | Japan . | |

OTHER PUBLICATIONS

Donald W. Breck, Structure, Chemistry, and Use John Wiley & Sons, New York, 1964, pp. 19–27.
Daniel S. Barker, the American Mineralogist, vol. 49, 1964, pp. 851–857.
Richard C. Erd, et al., the American Mineralogist, vol. 49, 1964, pp. 831–850.

Primary Examiner—Joseph L. Schofer
Assistant Examiner—Carmen B. Pili-Curtis
Attorney, Agent, or Firm—Jacobs & Jacobs

[57] ABSTRACT

An antibiotic zeolite and an antibiotic resin composition containing thereof are provided. The antibiotic zeolite is prepared by replacing all or a part of ion-exchangeable ions in zeolite with ammonium ions and antibiotic metal ions such as silver, copper, zinc, mercury, tin, lead, bismuth, cadmium, chromium and thallium. The antibiotic resin composition comprises the antibiotic zeolite and a resin such as polyethylene, polypropylene, polyvinyl chloride and polystyrene.

7 Claims, 4 Drawing Sheets

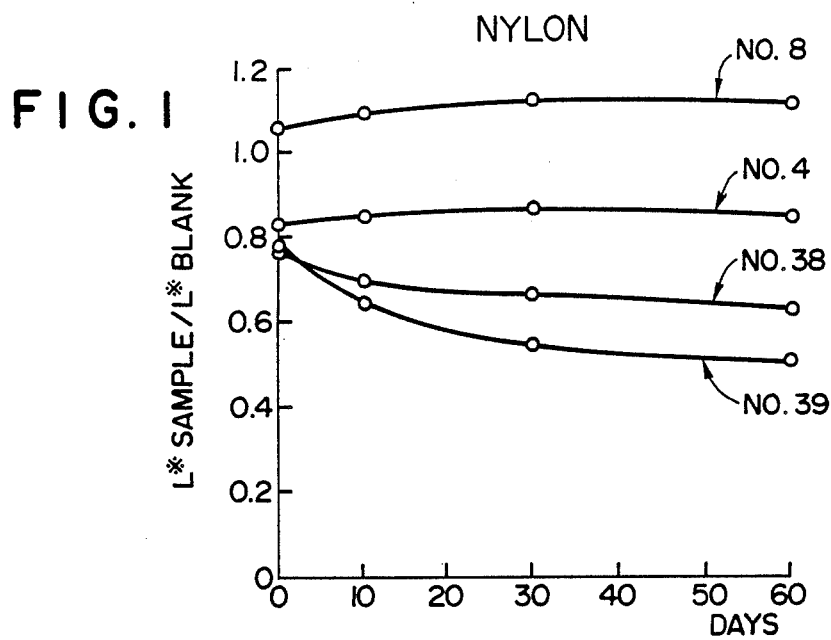
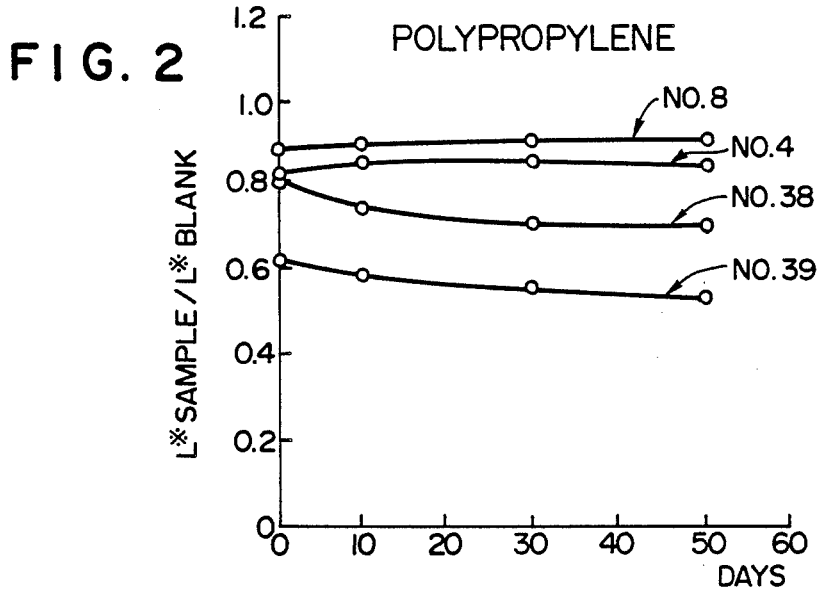

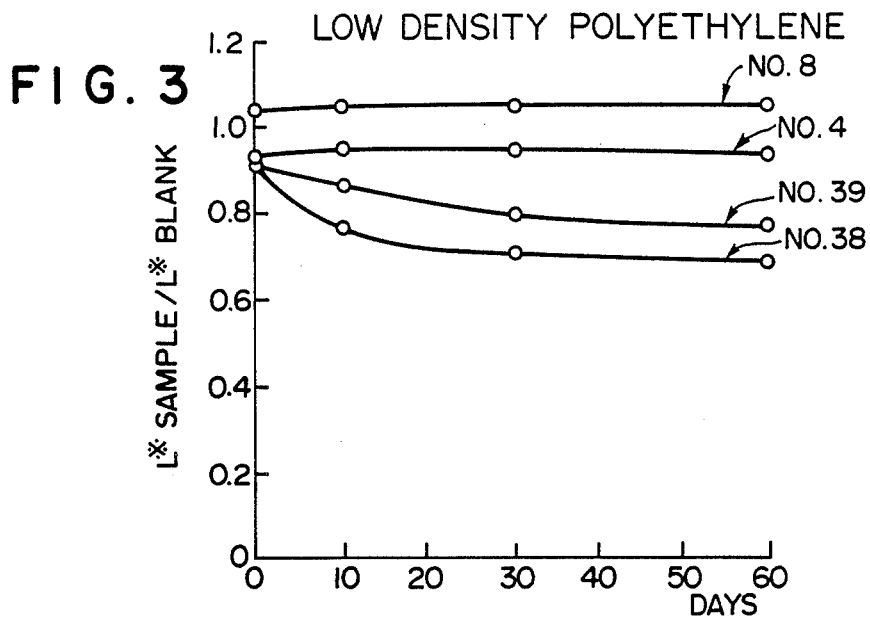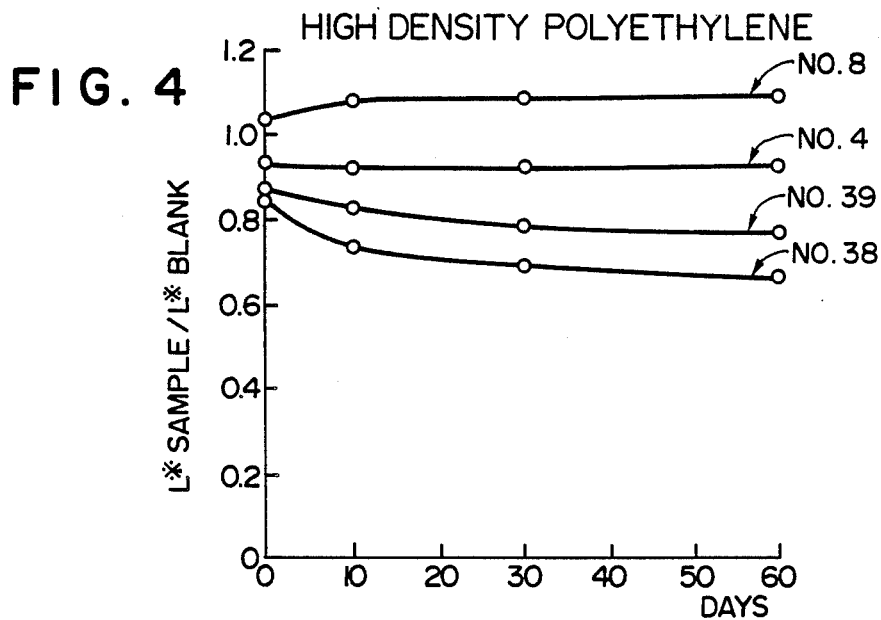

ANTIBIOTIC ZEOLITE

BACKGROUND OF THE INVENTION

1. Field of the Invention

The present invention relates to an antibiotic zeolite and an antibiotic resin composition containing the zeolite and more particularly to an antibiotic zeolite which does not cause discoloration with time.

2. Description of the Prior Art

Heretofore, there have been known such inorganic antibiotics as silver-supporting active carbon as disclosed in Japanese Patent Un-examined Publication No. 49-61950 and such organic antibacterial or antifungus agents as N-(fluorodichloromethylthio)-phthalimide.

However, in the former (inorganic antibiotics), silver ions are rapidly leached out therefrom and, therefore, it is difficult to attain a sustained antibiotic effect.

On the other hand, among the latter (organic antibacterial or antifungus agents), some of them have no antibacterial effect depending on the kinds of bacteria or mold (in other words, these being inferior in general purpose with respect to the kinds of bacteria or mold). Further even those having heat resistance sometimes cause decomposition or evaporation during kneading them into a resin at a temperature of 150° to 300° C. This leads to the reduction of antibacterial effect.

For the purpose of eliminating the aforementioned disadvantages associated with these conventional antibiotics, there have been developed so-called antibiotic zeolites which comprises an antibiotic component supported on zeolite (see, for instance, Japanese Patent Published for Opposition No. 61-22977 and Japanese Patent Un-examined Publication No. 60-181002).

The aforesaid antibiotic zeolite is certainly an excellent antibiotic agent which exhibits a sustained antibiotic action when left to stand in water or in the air and does not cause change of properties during kneading it with a resin. However, such an antibiotic zeolite suffers from a disadvantage that it gradually causes discoloration in the course of time. This discoloration exerts no influence on the antibiotic effect of the antibiotic zeolite and, therefore, the antibiotic zeolite is still an excellent antibiotic agent. However goods in which such an antibiotic zeolite is incorporated sometimes causes discoloration. This leads to remarkable reduction of their commercial value depending on the kinds thereof.

SUMMARY OF THE INVENTION

Accordingly, an object of the present invention is to provide an antibiotic zeolite which does not cause discoloration with time and which exhibits an excellent antibiotic effect high that of the conventional antibiotic zeolites.

Another object of the present invention is to provide an antibiotic resin composition comprising the antibiotic zeolite and a resin which does not cause discoloration with time.

The present invention relates to an antibiotic zeolite in which all or a part of ion-exchangeable ions in a zeolite are replaced with antibiotic metal and ammonium ions.

Further the present invention relates to an antibiotic resin composition comprises resin and an antibiotic zeolite in which all or a part of ion-exchangeable ions in zeolite being replaced with antibiotic metal and ammonium ions.

BRIEF DESCRIPTION OF THE DRAWINGS

FIGS. 1 to 7 show color change with the passage of time of Samples of resins into which the antibiotic zeolites of the invention is incorporated by kneading.

DESCRIPTION OF THE PREFERRED EMBODIMENT

Figure 5:
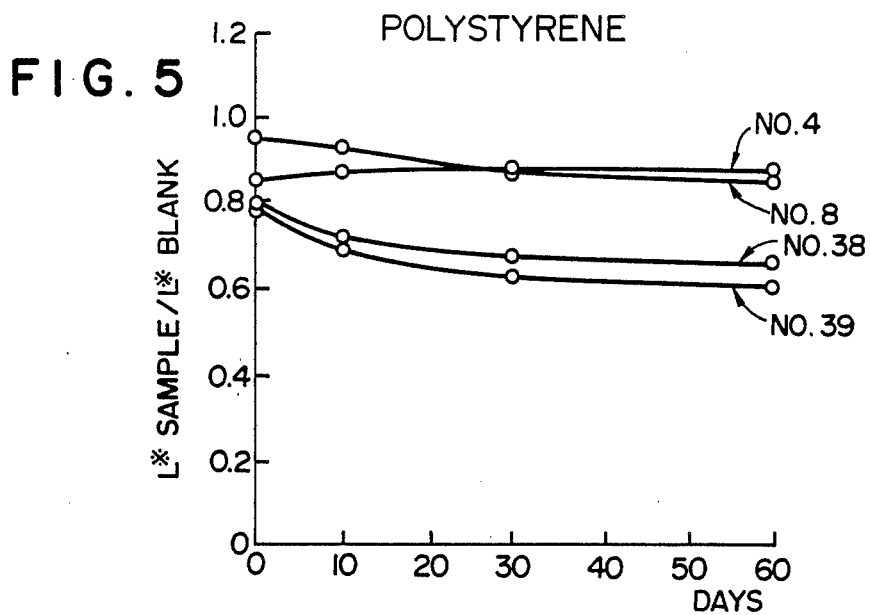

The present invention will hereunder be explained in more detail.

In the antibiotic zeolite of the present invention, either natural zeolites or synthetic zeolites may be used as "zeolite" component. Zeolite is in general aluminosilicate having a three dimensional skeletal structure and represented by the general formula: $XM2/nO-Al_2O_3-YSiO_2-ZH_2O$. In the general formula, M represents an ion-exchangeable ion and in general a monovalent or divalent metal ion, n represents atomic valency of the (metal) ion, X and Y represent coefficients of metal oxide and silica respectively, and Z represents the number of water of crystallization. Examples of such zeolites include A-type zeolites, X-type zeolites, Y-type zeolites, T-type zeolites, high-silica zeolites, sodalite, mordenite, analcite, clinoptilolite, chabazite and erionite. However, the present invention is not restricted to these specific examples. The ion-exchange capacities of these exemplified zeolite are as follows: A-type zeolite=7 meq/g; X-type zeolite=6.4 meq/g; Y-type zeolite=5 meq/g; T-type zeolite=3.4 meq/g; sodalite=11.5 meq/g; mordenite=2.6 meq/g; analcite=5 meq/g; clinoptilolite=2.6 meq/g; chabazite=5 meq/g; and erionite=3.8 meq/g. Thus, all the zeolites listed above have ion-exchange capacity sufficient to undergo ion-exchange with ammonium and antibiotic metal ions.

In the antibiotic zeolite of the present invention, ion-exchangeable ions present in zeolite, such as sodium ions, calcium ions, potassium ions and iron ions are completely or partially replaced with ammonium and antibiotic metal ions. Examples of the antibiotic metal ions include ions of silver, copper, zinc, mercury, tin, lead, bismuth, cadmium, chromium and thallium. Preferably the antibiotic metal ions are silver and copper or zinc ions. From the viewpoint of the antibiotic effect, in general the zeolite in the range of from 0.1 to 15% of the zeolite. In the present invention, it is preferable that the zeolite contains 0.1 to 15% of silver ions and 0.1 to 8% of copper or zinc ions. Although ammonium ion can be contained in the zeolite 20% or less of the zeolite, it is desirable to limit the content of ammonium ions in the zeolite to a range of from 0.5 to 15%, preferably 1.5 to 5% from the viewpoint of imparting an excellent antibiotic action thereto. In this connection, the term "%" herein means "% by weight" on the basis of the weight dried at 110° C.

Methods for preparing the antibiotic zeolite according to the present invention will hereunder be explained.

The antibiotic zeolite of the present invention may be obtained by bringing a zeolite into contact with a previously prepared aqueous mixed solution containing ammonium ions and antibiotic metal ions such as silver, copper and zinc ions to cause ion-exchange between ion-exchangeable ions in the zeolite and the aforesaid ions. The contact between these ions may be carried out according to a batch technique or a continuous technique (such as a column method) at a temperature of from 10° to 70° C., preferably from 40° to 60° C., for 3 to 24 hours, preferably 10 to 24 hours. In this respect, the pH value of the aqueous mixed solution is adjusted to 3 to 10, preferably 5 to 7 in view of preventing the silver oxide and the like from causing deposition on the surface of the zeolite or within the pores thereof. In addition, each of the ions are in general used in the form of a salt to prepare the aqueous mixed solution. For instance, there may be mentioned such an ammonium ion source as ammonium nitrate, ammonium sulfate and ammonium acetate; such a silver ion source as silver nitrate, silver sulfate, silver perchlorate, silver acetate, diamine silver nitrate and diamine silver nitrate; such a copper ion source as copper(II) nitrate, copper sulfate, copper perchlorate, copper acetate, tetracyan copper potassium; such a zinc ion source as zinc(II) nitrate, zinc sulfate, zinc perchlorate, zinc acetate and zinc thiocyanate; such a mercury ion source as mercury perchlorate, mercury nitrate and mercury acetate; such a tin ion source as tin sulfate; such a lead ion source as lead sulfate and lead nitrate; such a bismuth ion source as bismuth chloride and bismuth iodide; such a cadmium ion source as cadmium perchlorate, cadmium sulfate, cadmium nitrate and cadmium acetate; such a chromium ion source as chromium perchlorate, chromium sulfate, chromium ammonium sulfate and chromium acetate; and such a thallium ion source as thallium ion source as thallium perchlorate, thallium sulfate, thallium nitrate and thallium acetate.

The content of the ions such as ammonium ions in the zeolite may properly be controlled by adjusting the concentration of each ion species (or salt) in the aforesaid aqueous mixed solution. For example, if the antibiotic zeolite of the invention comprises ammonium and silver ions, the antibiotic zeolite having an ammonium ion content of 0.5 to 5% and a silver ion content of 0.1 to 5% can properly be obtained by bringing a zeolite into contact with an aqueous mixed solution having an ammonium ion concentration of 0.2 M/l to 2.5 M/l and a silver ion concentration of 0.002 M/l to 0.15 M/l. Moreover, if the antibiotic zeolite further comprises copper ions and zinc ions, the antibiotic zeolite having a copper ion content of 0.1 to 8% and a zinc ion content of 0.1 to 8% can properly be obtained by employing an aqueous mixed solution containing 0.1 M/l to 0.85 M/l of copper ions and 0.15 M/l to 1.2 M/l of zinc ions in addition to the aforementioned amounts of ammonium ions and silver ions.

Alternatively, the antibiotic zeolite according to the present invention may also be prepared by using separate aqueous solutions each containing single different ion species (or salt) and bringing a zeolite into contact with each solution one by one to cause ion-exchange therebetween. The concentration of each ion species in a specific solution can be determined in accordance with the concentrations of these ion species in the aforementioned aqueous mixed solution.

After completion of the ion-exchange, the zeolite thus treated is washed with water sufficiently followed by drying. The zeolite is preferably dried at a temperature of 105° to 115° C. under normal pressure or at a temperature of 70° to 90° C. under a reduced pressure (1 to 30 torr).

The antibiotic properties of the antibiotic zeolite of the present invention thus prepared may be estimated by determining the minimum growth inhibitory concentration (MIC) with respect to a variety of general bacteria, eumycetes and yeast.

In such a test, the bacteria listed below may be employed:

*Bacillus cereus* var mycoides, ATCC 11778
*Escherichia coli,* IFO 3301
*Pseudomonas aeruginosa,* IIDP-1
*Staphylococcus aureus,* ATCC 6538P
*Streptococcus faecalis,* RATCC 8043
*Aspergillus niger,* IFO 4407
*Aureobasiduim pullulans,* IFO 6353
*Chaetomium globosum,* ATCC 6205
*Gliocladium virens,* IFO 6355
*Penicillum funiculosum,* IFO 6345
*Candida albicans,* IFO 1594
*Saccharomyces cerevisiae,* IFO 1950

The test for determining MIC can be carried out by smearing a solution containing bacteria for innoculation to a plate culture medium to which a test sample of the antibiotic zeolite is added in any concentration and then culturing it. The MIC is defined as a minimum concentration thereof required for inhibiting the growth of each bacteria.

According to the present invention, an antibiotic resin composition is provided. The resin composition comprises the aforementioned antibiotic zeolite and resin.

Examples of the resin include a thermoplastic or thermosetting resin such as polyethylene, polypropylene, polyvinyl chloride, ABS resin, nylons, polyesters, polyvinylidene chloride, polyamides, polystyrene, polyacetals, polyvinyl alcohol, polycarbonate, acrylic resins, fluoroplastics, polyurethane elastomer, phenolic resins, urea resins, meramine resins, unsaturated polyester resins, epoxy resins, urethane resins, rayon, cuprammonium rayon, acetates, triacetates, vinylidene, natural or synthetic rubbers.

The resin composition is prepared by incorporating the antibiotic zeolite into the resin by means of kneading it with the zeolite or coating the antibiotic zeolite on the surface of such a resin in order to impart antibiotic, antifungus and anti-algal properties to each of these plastics. In order to provide antibacterial, antifungus and antialgal properties to a resin composition, the content of the antibiotic zeolite suitably ranges from 0.05 to 80 wt %, preferably 0.1 to 80 wt %. MIC of the antibiotic resin composition can be determined by the similar method to those of the anti biotic zeolite per se. Further, from the viewpoint of prevention of substantial discoloration of a resin composition containing the antibiotic zeolite of the present invention, the content of the antibiotic zeolite preferably ranges from 0.1 to 3 wt %.

The antibiotic zeolite according to the present invention may be applied to a variety of fields.

For example, in the field of water systems, the antibiotic zeolite of the present invention may be used as anti-algal agent in water cleaner, water of a cooling tour, and a variety of cooling water, or it may be used as an agent for prolonging life of cut flowers.

In the field of paints, the antibiotic zeolite of the present invention can impart antibiotic, antifungus and anti-algal properties to coated films by directly mixing the zeolite with various kinds of paints such as lyophilic paints, lacquer, varnish, and alkyl resin type, aminoalkyd resin type, vinyl resin type, acrylic resin type, epoxy resin type, urethane resin type, water type, powder type, chlorinated rubber type, phenolic paints; or by coating the zeolite on the surface of the coated films. In the field of construction, the antibiotic zeolite of the invention may impart antibiotic, antifungus and anti-algal properties to various parts for construction such as materials for joint and materials for wall and tile by admixing the zeolite with materials for parts for construction or applying the zeolite to the surface of such a material for construction.

In the field of paper making, the antibiotic zeolite of the invention may be incorporated into various paper materials such as wet tissue paper, paper packaging materials, corrugated boards, a sheet of paper, paper for maintaining freshness by papermaking from a material therefor together with the zeolite; or by coating the resultant paper with the zeolite for the purpose of imparting antibiotic and antifungus properties to these paper. Moreover, in the field of the papermaking, the antibiotic zeolite may also serves in particular as a slime controlling agent.

The antibiotic zeolite according to the present invention may be used in any fields in which the development and proliferation of microorganisms such as general bacteria, eumycetes and algae must be suppressed, in addition to the foregoing fields.

The present invention will hereunder be explained in more detail with reference to the following non-limitative working examples.

Example 1 (Method for preparing antibiotic zeolites)

In this Example, the following 11 kinds of zeolites were used: A-type zeolite ($Na_2O$-$Al_2O_3$-$1.9SiO_2$-$XH_2O$; average particle size=1.5 microns); X-type zeolite ($Na_2O$-$Al_2O_3$-$2.3SiO_2$—$XH_2O$; average particle size=2.5 microns); Y-type zeolite ($1.1Na_2O$-$Al_2O_3$—$4SiO_2$—$XH_2O$; average particle size=0.7 microns); natural mordenite (150 to 250 mesh); natural clinoptilolite (150 to 250 mesh); chabazite (150 to 250 mesh); erionite (150 to 250 mesh); T-type zeolite (2 microns); high-silica zeolite (5 microns); sadalite (2 microns): and analycite. As the source of each ion species required for ion-exchange, four kinds of salts: $NH_4NO_3$, $AgNO_3$, $Cu(NO_3)_2$, $Zn(NO_3)_2$, $Hg(NO_3)_2$, $Sn(NO_3)_2$, $Pb(NO_3)_2$, $Cd(NO_3)_2$ and $Cr(NO_3)_3$ were used.

Tables I-1 and I-2 show the details of the kinds of zeolite, the kinds of salts and their concentration in a mixed aqueous solution used to prepare Samples. Thus, 32 Samples of antibiotic zeolites were obtained.

Each Sample was prepared as follows: 1 kg of each zeolite powder which had been dried under heating at 110° C. was added to water to form 1.3 liters of slurry, then the slurry was stirred to degasify, proper amounts of 0.5N nitric acid solution and water were added thereto to adjust the pH to 5 to 7 and to thus obtain a slurry of a total volume of 1.8 liters. Thereafter, ion-exchange was carried out by adding, to the slurry, 3 liters of a mixed aqueous solution containing desired salts each present in a desired amount to obtain a slurry having a total volume of 4.8 liters and maintaining the slurry at a temperature of 40° to 60° C. for 10 to 24 hours while stirring to hold the slurry at an equilibrium state. After the ion-exchange was finished, the zeolite phase was filtered off followed by washing with water until almost no excess silver, copper or zinc ions remained in the zeolite phase. Then, Samples thus prepared were dried under heating at 110° C. and thus 32 Samples of the antibiotic zeolites were obtained. The data observed on these antibiotic zeolite Samples No. 1 to 32 are summarized in Tables I-1 and I-2.

Samples 33 and 34 were prepared as follows: 1 kg of A-type zeolite powder which had been dried under heating at 110° C. was added to absolute ethanol to form 1.3 liters of slurry and the resulting slurry was stirred to degasify. Then 0.1N of bismuth chloride in ethanol solution was added to the slurry to carry out ion-exchange and then stirred the slurry to hold the slurry at an equilibrium state. After the ion-exchange was finished, the zeolite phase was filtered off followed by washing with ethanol until almost no excess bismuth ions remained in the zeolite phase. Then, the resulting zeolite was dried to obtain Samples 33 and 34 of the antibiotic zeolite. The data observed on these antibiotic zeolite are summarized in Table I-2.

TABLE I

| Sample No. | Kind of zeolite | NH₄ | Ag | Cu | Zn | Yield (g) |
|---|---|---|---|---|---|---|
| 1 | A | 1.0 | 5.0 | — | — | 960 |
| 2 | A | 1.0 | 0.5 | — | — | 955 |
| 3 | A | 1.0 | 0.05 | — | — | 958 |
| 4 | A | 0.5 | 3.0 | 5.0 | — | 945 |
| 5 | X | 0.5 | 5.0 | 5.0 | — | 940 |
| 6 | X | 0.5 | 5.0 | 8.0 | — | 943 |
| 7 | Y | 1.0 | 5.0 | — | 2.5 | 910 |
| 8 | A | 1.0 | 5.0 | — | 5.0 | 906 |
| 9 | Y | 1.0 | 5.0 | — | 8.0 | 908 |
| 10 | Mordenite | 3.0 | 0.5 | 0.1 | — | 855 |
| 11 | Mordenite | 3.0 | 0.5 | 0.25 | — | 861 |
| 12 | Mordenite | 3.0 | 0.5 | 0.5 | — | 863 |
| 13 | Clinoptilolite | 0.8 | 0.5 | — | 0.1 | 900 |
| 14 | Clinoptilolite | 0.8 | 0.5 | — | 0.25 | 895 |
| 15 | Clinoptilolite | 0.8 | 0.5 | — | 0.40 | 901 |
| 16 | Chabazite | 3.0 | 0.05 | 0.025 | — | 880 |
| 17 | Chabazite | 3.0 | 0.05 | 0.05 | — | 893 |
| 18 | Chabazite | 3.0 | 0.05 | 0.10 | — | 885 |
| 19 | Erionite | 0.8 | 0.05 | — | 0.025 | 805 |
| 20 | Erionite | 0.8 | 0.05 | — | 0.05 | 811 |
| 21 | Erionite | 0.8 | 0.05 | — | 0.1 | 808 |
| 22 | A | 1.0 | 2.0 | 2.0 | 2.0 | 960 |

| Sample No. | Composition of mixed aq. solution (M/l) | | | | Solution pH | Ion-E time |
|---|---|---|---|---|---|---|
| | NH₄NO₃ | AgNO₃ | Cu(NO₃)₂ | Zn(NO₃)₂ | | |
| 1 | 1.5 | 0.05 | — | — | 6.1 | 10 hr |
| 2 | 1.5 | 0.015 | — | — | 5.0 | 15 hr |
| 3 | 1.5 | 0.0015 | — | — | 7.0 | 20 hr |
| 4 | 1.2 | 0.10 | 0.35 | — | 7.0 | 12 hr |
| 5 | 1.2 | 0.15 | 0.35 | — | 6.2 | 15 hr |
| 6 | 1.2 | 0.15 | 0.80 | — | 5.3 | 18 hr |
| 7 | 3.1 | 0.15 | — | 0.18 | 5.5 | 15 hr |
| 8 | 3.1 | 0.15 | — | 0.40 | 6.5 | 10 hr |
| 9 | 3.1 | 0.15 | — | 1.00 | 7.0 | 24 hr |
| 10 | 2.0 | 0.015 | 0.16 | — | 7.0 | 10 hr |
| 11 | 2.0 | 0.015 | 0.50 | — | 6.8 | 15 hr |
| 12 | 2.0 | 0.015 | 0.85 | — | 5.7 | 20 hr |
| 13 | 1.25 | 0.015 | — | 0.30 | 6.3 | 24 hr |
| 14 | 1.25 | 0.015 | — | 0.60 | 5.1 | 18 hr |
| 15 | 1.25 | 0.015 | — | 1.20 | 5.8 | 12 hr |
| 16 | 2.0 | 0.002 | 0.10 | — | 7.0 | 12 hr |
| 17 | 2.0 | 0.002 | 0.20 | — | 6.9 | 12 hr |
| 18 | 2.0 | 0.002 | 0.45 | — | 5.7 | 12 hr |
| 19 | 1.25 | 0.002 | — | 0.15 | 5.3 | 15 hr |
| 20 | 1.25 | 0.002 | — | 0.40 | 5.8 | 15 hr |
| 21 | 1.25 | 0.002 | — | 1.00 | 6.0 | 15 hr |
| 22 | 3.1 | 0.068 | 0.25 | 0.30 | 6.0 | 12 hr |

| Sample No. | Kind of zeolite | NH₄ | Ag | metal | Yield (g) |
|---|---|---|---|---|---|
| 23 | A | 1.0 | 2.8 | 3.2 (Hg) | 910 |
| 24 | A | 1.1 | 2.9 | 3.0 (Sn) | 930 |
| 25 | A | 0.8 | 2.7 | 4.1 (Pb) | 950 |
| 26 | A | 0.7 | 2.8 | 4.6 (Cd) | 940 |
| 27 | A | 0.6 | 2.6 | 4.3 (Cr) | 920 |
| 28 | A | 0.7 | 2.5 | 2.5 (Cr) | 890 |
| 29 | T | 0.7 | 3.8 | — | 950 |
| 30 | high-silica | 0.6 | 2.1 | — | 960 |
| 31 | sodalite | 1.4 | 3.2 | — | 950 |
| 32 | analcite | 1.3 | 3.1 | — | 970 |
| 33 | A | 0.4 | — | 1.9 | 950 |
| 34 | A | 0.4 | — | 2.8 | 930 |

| Sample No. | Composition of mixed aq. solution (M/l) | | | Slurry pH | Ion-Ex time |
|---|---|---|---|---|---|
| | NH₄NO₃ | AgNO₃ | Nitrate of metal | | |

TABLE I-continued

| | | | | | |
|---|---|---|---|---|---|
| 23 | 1.2 | 0.10 | 0.30 | 7.0 | 24 hr |
| 24 | 1.2 | 0.10 | 0.5 | 4.5 | 24 hr |
| 25 | 1.2 | 0.10 | 0.5 | 6.4 | 24 hr |
| 26 | 1.2 | 0.10 | 0.5 | 5.8 | 24 hr |
| 27 | 1.2 | 0.10 | 0.5 | 5.7 | 24 hr |
| 28 | 1.2 | 0.10 | 0.20 | 5.1 | 24 hr |
| 29 | 1.5 | 0.15 | — | 6.4 | 24 hr |
| 30 | 1.5 | 0.30 | — | 6.7 | 24 hr |
| 31 | 1.2 | 0.10 | — | 6.1 | 24 hr |
| 32 | 1.2 | 0.10 | — | 6.2 | 24 hr |
| 33 | 0.3 | — | 0.1 (BiCl) | — | 24 hr |
| 34 | 0.3 | — | 0.4 (BiCl) | — | 24 hr |

Example 2 (Test on Antibiotic Action)

The antibiotic action was estimated as follows:
The antibiotic action was determined on the following three strains: *Aspergillus niger* IFO 4407 (mold); *Candida albicans* IFO 1594 (yeast); and *Pseudomonas aeruginosa* IID P-1 (general bacteria).

As culture medium for proliferation of microorganisms, Mueller-Hinton Broth (Difco) for bacteria; Poteto Dextrose Agar Medium (Sakae Lab.) for mold; and Yeast Morphology Agar (Difco) for yeast were used. On the other hand, as medium for determining sensitivity, Mueller-Hinton Medium (Difco) for bacteria and Saburo Agar Medium (Sakae Lab.) for mold and yeast were used.

Plates for measuring sensitivity were prepared according in the following manner:

Each Sample was stepwise diluted with sterilized purified water to prepare a number of suspensions having different dilutions, each suspension thus prepared was added to the medium for measuring sensitivity, the temperature of which was raised up to temperature of 50° to 60° C. after dissolution, in an amount of 1/9 times volumes of the medium followed by sufficiently mixing, dispensing the product into petri dishes and solidifying the medium to form such plates for measuring sensitivity.

Bacteria solutions for inoculation were prepared as follows:

For bacteria: In this case, the bacteria solution was prepared by inoculating a test strain which had been subcultured on a medium for proliferation of bacteria, culturing it and diluting the medium with the same medium for proliferation of bacteria so that the number of bacterial cells was equal to $10^6$/ml.

For mold: The bacteria solution for proliferation of mold was prepared by inoculating a test strain which had been subcultured to a medium for proliferation of mold, culturing it and floating the resulting conidium on a sterilized solution of 0.05% polysorbate 80 so that the number of microorganisms was equal to $10^6$/ml.

For yeast: The solution for inoculation was prepared by inoculating a test strain which had been subcultured on a medium for proliferation of yeast, culturing it and floating the resulting cells of yeast on a sterilized physiologic saline so that the number of yeast cells was equal to $10^6$/ml.

Culture of each microorganism was carried out in the following manner:

The bacteria solution for inoculation was smeared on the plate for measuring sensitivity in the form of a line of 2 cm long with a loop of nichrome wire (inner diameter=about 1 mm) followed by culturing it at 37° C. for 18 to 20 hours for bacteria, at 25° C. for 7 days for mold. After culturing these for a desired time, the minimum growth inhibitory concentration (MIC) was determined as the concentration at which the growth of microorganisms was completely inhibited.

The results observed are summarized in Table II. In Table II, Sample No. 35 is a commertially available silver-supporting active carbon (supporting 1.4% Ag); and Sample No. 36 is a commertially available silver-supporting active carbon (supporting 0.6% Ag).

Moreover, Sample No. 37 is one for thermal resistance test, which was obtained by heating Sample No. 22 prepared in Example 1 at 350° C. for 3 hours in an electric furnace.

Sample No. 38 is one containing 3% of Ag and 5% of Cu obtained by subjecting an A-type zeolite to ion-exchange treatment. Sample No. 39 is one containing 2% of Ag and 10% of Zn obtained by subjecting an A-type zeolite to ion-exchange treatment. Samples Nos. 38 and 39 did not comprise ammonium ions al all.

TABLE II

| | Strains Tested | | |
|---|---|---|---|
| Sample No. | Pseudomonas aeruginosa IID P-1 | Aspergillus niger IFO 4407 | Candida albicans IFO 1594 |
| 1 | 62.5 | 500 | 250 |
| 2 | 2000 | 2000 | 2000 |
| 4 | 250 | 250 | 250 |
| 5 | 250 | 250 | 250 |
| 6 | 125 | 250 | 250 |
| 7 | 125 | 500 | 250 |
| 8 | 125 | 500 | 250 |
| 9 | 125 | 250 | 250 |
| 10 | 1000 | 2000 | 2000 |
| 11 | 2000 | 2000 | 2000 |
| 12 | 2000 | 2000 | 2000 |
| 13 | 1000 | 2000 | 2000 |
| 14 | 2000 | 2000 | 2000 |
| 15 | 1000 | 2000 | 2000 |
| 22 | 125 | 500 | 250 |
| 23 | 62.5 | 125 | 125 |
| 24 | 1000 | 1000 | 2000 |
| 25 | 1000 | >2000 | 1000 |
| 26 | 500 | 1000 | 500 |
| 27 | 1000 | >2000 | 2000 |
| 28 | 125 | 250 | 62.5 |
| 33 | 2000 | 2000 | 500 |
| 35 | 1000 | 2000 | 2000 |
| 36 | 1000 | 2000 | 2000 |
| 37 | 125 | 1000 | 250 |
| 38 | 125 | 1000 | 500 |
| 39 | 125 | 1000 | 250 |

Example 3 (Anti-algal Test)

Three aqueous solutions were prepared by adding 1 liter each of water to cylindrical 2-liter volume of containers of glass and then adding a desired amount of each Sample thereto to form a solution containing 2 g of Sample No. 1, a solution containing 2 g of Sample No. 4 and an aqueous solution free from samples (blank). These solutions were left to stand for 4 months and were visually observed on whether algae was developed or not. In order to prevent, from lowering, the water level due to the evaporation, water was properly replenished to each container. The results thus observed are summarized in Table III below.

TABLE III

| Time elapsed (days) | No. 1 | No. 4 | Blank |
|---|---|---|---|
| 0 | — | — | — |
| 15 | — | — | mold was developed in some degree at water surface and the container surface |

TABLE III-continued

| Time elapsed (days) | No. 1 | No. 4 | Blank |
|---|---|---|---|
| 30 | — | — | mold was developed on all the container surface below the water level |
| 45 | — | — | mold was also developed in water |
| 60 | — | — | |
| 90 | — | — | |
| 120 | — | — | |

—: Development of mold was not observed;
Sample No. 1: A-type; $NH_4$ 1.0%; Ag 5.0%
Sample No. 4: A-type; $NH_4$ 0.5%; Ag 3.0%; Cu 5.0%

Example 4 (Test on the Amount of silver ions Leach Out)

Sample No. 1 (in the form of pellets of ⅛ and 1/16) was charged in a column of pyrex in an amount of 8.1 g and then tap water was passed therethrough and water samples were collected at a time when 10, 50, 100 or 200 liters of water was passed through the column to determine the concentration of silver ions in each water sample. Such procedures were repeated 3 times. The results obtained are listed in Table IV given below.

TABLE IV

| Number of Experiments | Amount of Water Passed through the Column (liter) | | | |
|---|---|---|---|---|
| | 10 | 50 | 100 | 200 |
| 1 | 3 | 2 | 2 | 1 |
| 2 | 2 | 2 | 1 | 1 |
| 3 | 3 | 2 | 1 | 1 |
| Average | 2.7 | 2 | 1.3 | 1 |

*: The amount of silver ions are expressed as ppb.
Sample No.1: A-type zeolite; $NH_4$ 1.0%; Ag 5.0%
Column Used: 20 mm (ID) × 100 mm
Flow Rate: 100 ml/min Temperature: Room Temperature It was confirmed that the amount of silver ions dissolved in running water was quite low.

Example 5 (Test on Discoloration)

Figure 6:
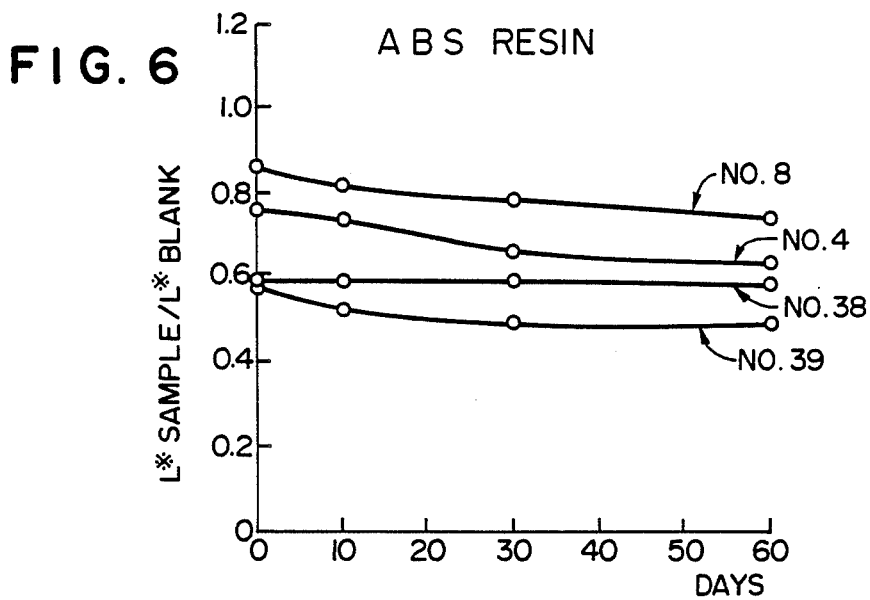
Figure 7:
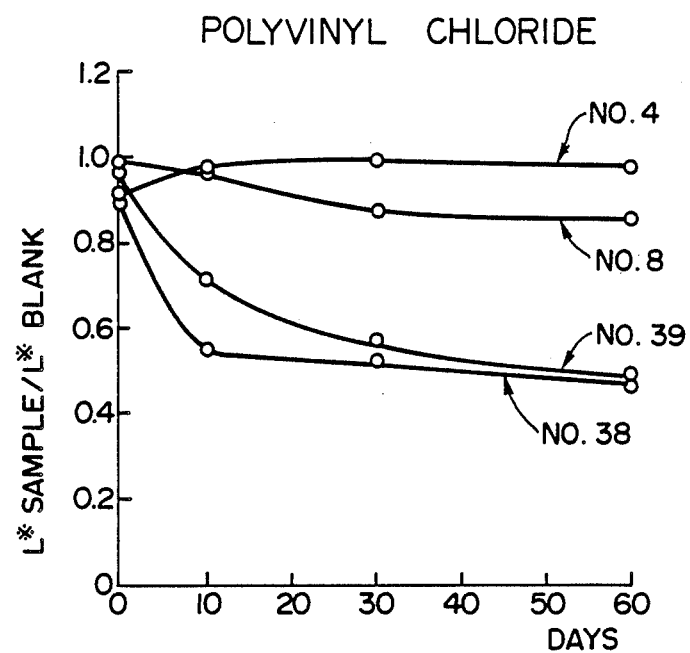

Samples of antibiotic zeolite which had been dried under heating were added to a resin by kneading in an amount of 1% by weight and the resultant products were injection-molded (residence time=2 min) (size of pieces=7.3 cm×4.4 cm×2 mm). The resultant Samples were exposed to sunlight in the air. The color of Samples was determined by placing each Sample on a white Kent paper ($L^*a^*b^*$ 93.1; −0.7; −0.5) with Minolta color-color difference meter CR-100 (using D65 rays; see Table VI). In this connection, the color of the antibiotic zeolite per se was determined by packing each zeolite in a petri dish of glass (diameter=150 mm) while vibrating the petri dish so that the height thereof in the dish was 2 cm (the results obtained were listed in Table V). These results are expressed in accordance with $L^*a^*b^*$ colorimetric system (CIE 1976). In addition, the results on $L^*$ in Table VI are shown in the attached FIGS. 1 to 7.

(Samples of antibiotic zeolites)

No. 4: A-type; $NH_4$ 0.5%; Ag 3.0%; Cu 5.0%
No. 38: A-type; Ag 3.0%; Cu 5.0%
No. 8: A-type; $NH_4$ 1.0%; Ag 5.0%; Zn 5.0%
No. 39: A-type; Ag 2.0%; Zn 10.0%

(Resins)

Nylon Novamid 1010J (manufactured and sold by MITSUBISHI CHEMICAL INDUSTRIES LTD.)
Polypropylene: J-109G (manufactured and sold Industries, Ltd.)
Low Density: Suntec F-1920 (manufactured and sold by Asahi Polyethylene Chemical Industry Co., Ltd.)
High Density: Suntec HDS-360 (manufactured and sold by Asahi Polyethylene Chemical Industry Co., Ltd.)
Polystyrene: GH 9600 (manufactured and sold by DAINIPPON INK AND CHEMICALS, INC.)
ABS Resin: GTR-10 (manufactured and sold by DENKI KAGAKU KOGYO KABUSHIKI KAISHA)
Vinyl Chloride: B-3050F2 (manufactured and sold by DENKI KAGAKU KOGYO KABUSHIKI KAISHA)

(Added DOP 60 Parts)

TABLE V

| Antibiotic Zeolite | $L^*$ | $a^*$ | $b^*$ |
|---|---|---|---|
| No. 4 | 90.9 | −7.3 | −7.2 |
| No. 38 | 91.1 | −8.0 | −4.7 |
| No. 8 | 97.3 | −1.6 | −1.8 |
| No. 39 | 95.5 | −1.8 | −5.2 |

*: Each Sample was previously dried under heating at 110° C.

TABLE VI

| Sample No. | Heating Conditions Before Kneading Temp (deg. C.) | Heating Conditions Before Kneading Time (hr.) | Injection-Molding Temp. (degree C.) | $L^*$ 0 day | $a^*$ 0 day | $b^*$ 0 day | $L^*$ 10 days | $a^*$ 10 days | $b^*$ 10 days | $L^*$ 30 days | $a^*$ 30 days | $b^*$ 30 days | $L^*$ 60 days | $a^*$ 60 days | $b^*$ 60 days |
|---|---|---|---|---|---|---|---|---|---|---|---|---|---|---|---|
| (nylon) | | | | | | | | | | | | | | | |
| No. 4 | 280 | 3 | 280 | 64.8 | −9.5 | −6.8 | 64.8 | −9.4 | −5.5 | 63.0 | −9.3 | −4.0 | 61.2 | −9.3 | −2.1 |
| No. 38 | 280 | 3 | 280 | 60.0 | 0.7 | 18.6 | 52.0 | 2.4 | 19.8 | 48.9 | 2.7 | 20.7 | 45.2 | 3.2 | 21.1 |
| No. 8 | 280 | 3 | 280 | 81.9 | −2.5 | 10.0 | 81.6 | −2.4 | 10.5 | 81.0 | −2.2 | 11.1 | 80.0 | −2.0 | 12.0 |
| No. 39 | 280 | 3 | 280 | 53.2 | 3.8 | 22.7 | 48.9 | 4.4 | 23.1 | 40.2 | 4.9 | 24.8 | 37.2 | 5.1 | 25.5 |
| blank | — | — | 280 | 78.2 | −0.5 | 3.2 | 75.1 | 0.1 | 4.2 | 72.6 | 0.2 | 6.5 | 72.3 | 0.2 | 6.7 |
| (polypropylene) | | | | | | | | | | | | | | | |
| No. 4 | 260 | 3 | 260 | 64.5 | −10.6 | 0.2 | 64.0 | −9.8 | 1.5 | 63.5 | −8.6 | 4.3 | −61.7 | −6.4 | 8.7 |
| No. 38 | 260 | 3 | 260 | 48.3 | 2.5 | 28.6 | 44.0 | 3.0 | 29.5 | 41.2 | 3.6 | 30.7 | 39.1 | 3.8 | 31.1 |
| No. 8 | 260 | 3 | 260 | 68.3 | −0.8 | 7.2 | 67.6 | −0.7 | 8.9 | 66.4 | −0.7 | 11.5 | 66.2 | −0.7 | 12.1 |
| No. 39 | 260 | 3 | 260 | 63.8 | −0.7 | 18.1 | 56.0 | 1.5 | 19.4 | 52.4 | 2.1 | 20.0 | 51.7 | 2.6 | 20.5 |
| blank | — | — | 260 | 77.6 | −0.4 | 3.2 | 74.7 | 0.1 | 4.5 | 73.5 | 0.4 | 4.7 | 73.0 | 0.5 | 5.1 |
| (low density polyethylene) | | | | | | | | | | | | | | | |
| No. 4 | 220 | 3 | 220 | 65.9 | −6.3 | −8.2 | 64.9 | −6.3 | −5.3 | 63.8 | −6.3 | −2.9 | 63.2 | −6.3 | −2.2 |
| No. 38 | 220 | 3 | 220 | 64.4 | −7.9 | 11.4 | 52.8 | −3.3 | 14.5 | 48.6 | −1.8 | 16.3 | 46.0 | 0.2 | 18.5 |

TABLE VI-continued

| Sample No. | Heating Conditions Before Kneading Temp (deg. C.) | Time (hr.) | Injection-Molding Temp. (degree C.) | L* | a* | b* | L* | a* | b* | L* | a* | b* | L* | a* | b* |
|---|---|---|---|---|---|---|---|---|---|---|---|---|---|---|---|
| | | | | | 0 day | | | 10 days | | | 30 days | | | 60 days | |
| No. 8 | 220 | 3 | 220 | 73.3 | −3.0 | 7.4 | 71.9 | −4.5 | 13.1 | 71.0 | −5.0 | 15.9 | 70.6 | −5.1 | 18.0 |
| No. 39 | 220 | 3 | 220 | 63.8 | −0.6 | 17.9 | 59.4 | 1.5 | 18.8 | 54.6 | 2.2 | 19.6 | 52.4 | 2.4 | 20.4 |
| blank | — | — | 220 | 70.7 | −1.1 | 3.3 | 68.6 | 1.8 | 4.6 | 68.0 | 2.2 | 6.0 | 67.7 | 2.5 | 7.1 |
| (high density polyethylene) | | | | | | | | | | | | | | | |
| No. 4 | 240 | 3 | 240 | 70.9 | −6.1 | −6.7 | 68.0 | 6.1 | −3.8 | 67.2 | 6.1 | −2.4 | 66.5 | −6.0 | −2.0 |
| No. 38 | 240 | 3 | 240 | 66.5 | −7.1 | 10.9 | 55.0 | −2.9 | 13.9 | 50.5 | −1.5 | 15.5 | 48.2 | 0.2 | 17.7 |
| No. 8 | 240 | 3 | 240 | 81.6 | −0.2 | 5.5 | 80.1 | −0.3 | 8.8 | 79.2 | −0.3 | 11.5 | 78.7 | −0.3 | 12.9 |
| No. 39 | 240 | 3 | 240 | 68.6 | −0.5 | 13.8 | 61.2 | 1.0 | 15.7 | 57.2 | 2.0 | 17.6 | 55.6 | 2.6 | 18.1 |
| blank | — | — | 240 | 78.5 | −1.6 | −3.1 | 74.0 | 1.2 | 1.2 | 73.1 | 1.8 | 2.9 | 72.8 | 2.2 | 3.5 |
| (polystyrene) | | | | | | | | | | | | | | | |
| No. 4 | 230 | 3 | 230 | 72.7 | −9.9 | 1.1 | 71.4 | −9.5 | 0 | 70.8 | −8.9 | −0.7 | 69.6 | −8.6 | −1.3 |
| No. 38 | 230 | 3 | 230 | 68.6 | −5.0 | 16.2 | 58.3 | −3.3 | 8.2 | 54.5 | −1.3 | 4.8 | 51.7 | 0 | 1.5 |
| No. 8 | 230 | 3 | 230 | 81.6 | −2.6 | 11.1 | 75.7 | −1.3 | 13.4 | 70.5 / −0.9 | | 14.9 | 68.6 | −0.6 | 15.2 |
| No. 39 | 230 | 3 | 230 | 66.8 | −1.5 | 11.3 | 55.9 | −0.2 | 10.5 | 50.3 | 0.8 | 9.4 | 47.7 | 1.0 | 9.0 |
| blank | — | — | 230 | 85.9 | −2.0 | −3.4 | 80.9 | 0 | −1.2 | 79.9 | 0.7 | 1.5 | 78.6 | 1.1 | 2.5 |
| (ABS resin) | | | | | | | | | | | | | | | |
| No. 4 | 250 | 3 | 250 | 61.8 | −3.8 | 1.5 | 56.7 | −2.4 | 2.9 | 52.2 | −1.8 | 4.9 | 49.5 | −1.6 | 5.1 |
| No. 38 | 250 | 3 | 250 | 48.1 | −0.3 | 2.0 | 46.4 | −0.1 | 3.1 | 45.9 | 0 | 4.4 | 45.3 | 0 | 4.7 |
| No. 8 | 250 | 3 | 250 | 69.9 | −1.9 | 13.4 | 63.5 | 1.0 | 12.9 | 60.5 | 0.8 | 10.2 | 59.6 | −0.7 | 8.4 |
| No. 39 | 250 | 3 | 250 | 46.9 | 0.4 | 3.5 | 40.6 | 0.4 | 3.5 | 38.1 | 0.5 | 3.5 | 37.5 | 0.6 | 3.4 |
| blank | — | — | 250 | 81.0 | −4.2 | 12.3 | 78.3 | −2.5 | 13.8 | 78.0 | −0.4 | 14.2 | 77.0 | −0.2 | 14.5 |
| (vinyl chloride) | | | | | | | | | | | | | | | |
| No. 4 | 180 | 3 | 180 | 66.9 | −7.9 | −1.2 | 64.7 | 6.6 | 1.2 | 62.3 | −5.7 | 4.6 | 60.8 | −5.1 | 8.7 |
| No. 38 | 180 | 3 | 180 | 68.5 | −7.5 | −0.8 | 36.3 | −0.1 | 4.2 | 33.5 | 0.7 | 10.5 | 30.1 | 1.2 | 15.3 |
| No. 8 | 180 | 3 | 180 | 73.4 | −2.4 | 7.3 | 63.1 | 0 | 15.5 | 55.1 | 2.3 | 21.1 | 53.1 | 4.1 | 25.5 |
| No. 39 | 180 | 3 | 180 | 72.0 | −2.2 | 6.5 | 47.0 | 4.7 | 20.6 | 36.1 | 5.2 | 25.5 | 28.6 | 8.6 | 35.0 |
| blank | — | — | 180 | 74.5 | 0.2 | 4.1 | 65.9 | 0.9 | 6.1 | 63.2 | 1.7 | 9.2 | 62.8 | 2.8 | 12.1 |

Effects of the Invention

The antibiotic zeolite according to the present invention exhibits an antibiotic action as good as that of the conventional antibiotic zeolite and extremely low change in color as compared with that of the conventional product. Therefore, the antibiotic zeolite of the invention is greatly improved in its properties. Moreover, the amount of silver leached out therefrom is also very low compared with the conventional ones due to the presence of ammonium ions.

We claim:

1. An antibiotic resin composition, which comprises a resin and from 0.05 to 80 wt % of an antibiotic zeolite in which all or a part of ion-exchangable ions in said zeolite are replaced with antibiotic metal ions comprising silver ions and with ammonium ions, the amount of silver ions ranging from 0.1 to 15 wt % and the amount of ammonium ions ranging from 0.5 to 15 wt %.

2. An antibiotic resin composition according to claim 1 wherein the resin is at least one member selected from the group consisting of polyethylene, polypropylene, polyvinyl chloride, ABS resin, nylons, polyesters, polyvinylidene chloride, polyamides, polystyrene, polyacetals, polyvinyl alcohol, polycarbonate, acrylic resins, fluoroplastics, polyurethane elastomer, phenolic resins, urea resins, meramine resins, unsaturated polyester resins, epoxy resins, urethane resins, rayon, cuprammonium rayon, acetates, triacetates, vinylidene, natural or synthetic rubbers.

3. An antibiotic resin composition according to claim 1 wherein the content of the antibiotic zeolite ranges from 0.1 to 80 wt %.

4. An antibiotic resin composition according to claim 3 wherein the content of the antibiotic zeolite ranges from 0.1 to 3 wt %.

5. An antibiotic resin composition according to claim 1 wherein the antibiotic metal ions are silver ions and at least one ion of metals selected from the group consisting of copper, zinc, mercury, tin, lead, bismuth, cadmium, chromium and thallium.

6. An antibiotic resin composition according to claim 5 wherein the antibiotic metal ions are silver ions or are silver ions and copper or zinc ions.

7. An antibiotic resin composition according to claim 6 wherein the content of copper ions, when present, ranges from 0.1 to 8 wt % and the content of zinc, when present, ranges from 0.1 to 8 wt %.

* * * * *